(12) United States Patent
Aikawa et al.

(10) Patent No.: US 10,190,119 B2
(45) Date of Patent: Jan. 29, 2019

(54) MITOCHONDRIAL PHOSPHATE CARRIER TARGETS FOR TREATING SOFT-TISSUE CALCIFICATION

(71) Applicant: THE BRIGHAM AND WOMEN'S HOSPITAL, INC., Boston, MA (US)

(72) Inventors: Elena Aikawa, Chestnut Hill, MA (US); Joshua Daniel Hutcheson, Allston, MA (US); Claudia Goettsch, Brookline, MA (US); Masanori Aikawa, Chestnut Hill, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 0 days.

(21) Appl. No.: 15/527,568

(22) PCT Filed: Nov. 17, 2015

(86) PCT No.: PCT/US2015/061008
§ 371 (c)(1),
(2) Date: May 17, 2017

(87) PCT Pub. No.: WO2016/081419
PCT Pub. Date: May 26, 2016

(65) Prior Publication Data
US 2017/0355988 A1    Dec. 14, 2017

Related U.S. Application Data

(60) Provisional application No. 62/080,657, filed on Nov. 17, 2014.

(51) Int. Cl.
*C12N 15/113*    (2010.01)
*A61K 31/713*    (2006.01)
*A61K 45/06*    (2006.01)

(52) U.S. Cl.
CPC .......... *C12N 15/113* (2013.01); *A61K 31/713* (2013.01); *A61K 45/06* (2013.01); *C12N 2310/14* (2013.01)

(58) Field of Classification Search
CPC .................................................. A61K 48/00
See application file for complete search history.

(56) References Cited

U.S. PATENT DOCUMENTS

2011/0263675 A1    10/2011 Federov

OTHER PUBLICATIONS

Li, Zhifu, et al. "Mitochondrial genome sequencing of chondrocytes in osteoarthritis by human mitochondria RT2 Profiler™ PCR array." Molecular medicine reports 6.1 (2012): 39-44.*
Aikawa et al., "Multimodality molecular imaging identifies proteolytic and osteogenic activities in early aortic valve disease", Circulation 115(3) 377-386 (2007).
Aikawa et al., "Osteogenesis associates with inflammation in early-stage atherosclerosis evaluated by molecular imaging in vivo", Criculation 116(24) 2841-2850 (2007).
Baseler et al., "miR-141 as a regulator of the mitochondrial phosphate carrier (Slc25a3) in the type 1 diabetic heart", Am J Physiol Cell Physiol 303(12) C1244-C1251 (2012).
Gkizas et al., "Aldosterone receptor blockade inhibits degenerative processes in the early stage of calcific aortic stenosis", Eur J Pharmacol 642(1-3) 107-112 (2010).
Jaffe et al., "Mineralocorticoid receptor activation promotes vascular cell calcification", Arterioscler Thromb Vasc Biol 27(4) 799-805 (2007).
Kwong et al., "Genetic deletion of the mitochondrial phosphate carrier desensitizes the mitochondrial permeability transition pore and causes cardiomyopathy", Cell Death Differ 21(8) 1209-1217 (2014).
Monzack et al., "Efficacy of simvastatin treatment of valvular interstitial cells varies with the extracellular environment", Arterioscler Thromb Vasc Biol 29(2) 246-253 (2009).
Osman et al., "A novel role of extracellular nucleotides in valve calcification: a potential target for atorvastatin", circulation 114(1 Suppl) 1566-1572 (2006).
Osman et al., "Role of human valve interstitial cells in valve calcification and their response to atorvastatin", Circulation 114(1 Suppl) I547-I552 (2006).
Perovic et al., "A pearl protein self-assembles to form protein complexes that amplify mineralization", Biochemistry 52(33) 5696-5703 (2013).
Rajamannan et al., "Atorvastatin inhibits hypercholesterolemia-induced calcification in the aortic valves via the Lrp5 receptor pathway", Circulation 112(9 Suppl) 1229-1234 (2005).
Traba et al., "SCaMC-1 promotes cancer cell survival by desensitizing mitochondrial permeability transition via ATP/ADP-mediated matrix Ca(2+) buffering", Cell Death Differ 19(4) 650-660 (2012).
Yanagawa et al., "mlRNA-141 is a novel regulator of BMP-2—mediated calcification in aortic stenosis", Journal of Thoracis and Cardiovascular Surgery 144(1) 256-262 (2012).
Yang et al., "A self-sequestered calmodulin-like $Ca^{2+}$ sensor of mitochondrial SCaMC carrier and its implication to $Ca^{2+}$-dependent ATP-Mg/P(i) transport", Structure 22(2) 209-217 (2014).

* cited by examiner

*Primary Examiner* — Kimberly Chong
(74) *Attorney, Agent, or Firm* — Nixon Peabody LLP; David S. Resnick; Mark J. FitzGerald

(57) ABSTRACT

Disclosed herein are compositions and methods for treating soft-tissue calcification by targeting SLC25A24 and/or SLC25A3.

4 Claims, 4 Drawing Sheets
Specification includes a Sequence Listing.

SEQUENCE LISTING

```
<160> NUMBER OF SEQ ID NOS: 8

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
cagaugaauu cacggaaga                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gcauaugaac aguacaaga                                                  19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaaauggua caaacguca                                                  19

<210> SEQ ID NO 4
<211> LENGTH: 19
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 4
ggugcugucu cucgaacaa                                                   19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gggcauauuu aacggauuc                                                   19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uggcgcacau cacuauauu                                                   19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcaauuguuu cucacccug                                                   19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gccaacacuu ugagggaug                                                   19
```

MITOCHONDRIAL PHOSPHATE CARRIER TARGETS FOR TREATING SOFT-TISSUE CALCIFICATION

CROSS REFERENCE TO RELATED APPLICATIONS

This Application is a 35 U.S.C. § 371 National Phase Entry Application of International Application No. PCT/US2015/061008 filed Nov. 17, 2015, which designates the U.S. and which claims benefit under 35 U.S.C. § 119(e) of the U.S. Provisional Application No. 62/080,657 filed Nov. 17, 2014, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 7, 2015, is named 043214-083571-PCT_SL.txt and is 2,216 bytes in size.

TECHNICAL FIELD

The present disclosure relates to treatment of conditions resulting from soft-tissue calcification.

BACKGROUND

Soft-tissue calcification occurs when calcium and other mineral salts are deposited in a tissue. Calcification of soft tissues plays a major role in the pathologies of a variety of diseases such as macular degeneration, cancer, kidney disease, and cardiovascular disease. In particular, arterial and valvular calcification promotes heart attacks and aortic valve stenosis, which represent major health problems and economic burden in the United States.

Cardiovascular calcification is a disease of dysregulated mineral metabolism, which leads to increased cardiovascular events and potentially death. Microcalcifications located in the thin fibrous cap overlying the necrotic core of atherosclerotic plaques may cause microfractures, which can lead to acute thrombosis and even sudden death due to fatal acute myocardial infarction (Huang H, Circulation, 2001; Virmani R, 2006; Vengrenyuk Y, 2006). Various therapeutic agents have been investigated to target cardiovascular calcification; these include statins (Aikawa E, Circulation, 2007; Monzack et al, 2009; Osman L, Circulation, 2006; Rajamannan N M, Circulation, 2005) and mineralocorticoid receptor antagonists (Gkizas S, Cardiovasc. Pharma, 2010; Jaffe I Z, ATVB, 2007), however as yet they have not proved beneficial in the clinical setting (Gilmanov D, Inter. Cardiovasc Thor Surg. 2010).

Accordingly, there is an unmet need in the art for new methods for the treatment of soft-tissue calcification including, but not limited to, cardiovascular calcification.

SUMMARY

The invention is based, in part, on the discovery that SLC25A24 (i.e. solute carrier family 25, member 24, or SCaMC-1) and SLC25A3 (i.e. solute carrier family 25, member 3, or PiC) proteins are implicated in the calcification process of soft tissues. More specifically, it was discovered that SLC25A24 and SLC25A3 proteins play a role in the formation of calcium phosphate mineral within the vesicles. Based on this discovery, inhibition of SLC25A24 and/or SLC25A3 can thus be exploited to treat soft-tissue calcification.

One aspect of the technology described herein relates to a method of treating soft-tissue calcification in a subject, the method comprising administering a therapeutically-effective amount of an SLC25A24 inhibitor to the subject.

In one embodiment, the soft-tissue calcification occurs in a soft tissue selected from the group consisting of an artery, a heart valve, an eye, a visceral organ, and skin.

In one embodiment, the SLC25A24 inhibitor decreases the expression level of SLC25A24 protein.

In one embodiment, the SLC25A24 inhibitor decreases the ability of SLC25A24 protein to transport phosphate into matrix vesicles.

In one embodiment, the SLC25A24 inhibitor is selected from the group consisting of a small or large organic or inorganic molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and combinations thereof.

In one embodiment, the SLC25A24 inhibitor is a small interfering RNA (siRNA).

In one embodiment, the small siRNA for SLC25A24 is selected from the group consisting of CAGAUGAAUU-CACGGAAGA (SEQ ID NO: 1), GCAUAUGAACAGUA-CAAGA (SEQ ID NO: 2), GGAAAUGGUACAAAC-GUCA (SEQ ID NO: 3), GGUGCUGUCUCUCGAACAA (SEQ ID NO: 4), and a combination thereof.

In one embodiment, the method further comprises administering a therapeutically-effective amount of an SLC25A3 inhibitor to the subject.

In one embodiment, the subject is a mammal.

In one embodiment, the mammal is a human.

One aspect of the technology described herein relates to a method of treating soft-tissue calcification in a subject, the method comprising administering a therapeutically-effective amount of an SLC25A3 inhibitor to the subject.

In one embodiment, the soft-tissue calcification occurs in a soft tissue selected from the group consisting of an artery, a heart valve, an eye, a visceral organ, and skin.

In one embodiment, the SLC25A3 inhibitor decreases the expression level of SLC25A3 protein.

In one embodiment, the SLC25A3 inhibitor decreases the ability of SLC25A3 protein to transport phosphate into matrix vesicles.

In one embodiment, the SLC25A3 inhibitor is selected from the group consisting of a small or large organic or inorganic molecule, a nucleic acid, a nucleic acid analog or derivative, a peptide, a peptidomimetic, a protein, an antibody or an antigen-binding fragment thereof, a monosaccharide, a disaccharide, a trisaccharide, an oligosaccharide, a polysaccharide, a lipid, a glycosaminoglycan, an extract made from a biological material, and any combinations thereof.

In one embodiment, the SLC25A3 inhibitor is a small interfering RNA (siRNA).

In one embodiment, the siRNA for SLC25A3 is selected from the group consisting of GGGCAUAUUUAACG-GAUUC (SEQ ID NO: 5), UGGCGCACAUCAC-UAUAUU (SEQ ID NO: 6), GCAAUUGUUUCUCAC-CCUG (SEQ ID NO: 7), GCCAACACUUUGAGGGAUG (SEQ ID NO: 8), and a combination thereof.

In one embodiment, the subject is a mammal.

In one embodiment, the mammal is a human.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

As used herein, the term "SLC25A24" generally refers to a SLC25A24 polypeptide or a SLC25A24 polynucleotide. When referring to the inhibition of SLC25A24, it means, at a minimum, the inhibition of the expression level and/or activity of SLC25A24 that corresponds to NCBI Gene ID: 29957.

As used herein, the terms "inhibitor of SLC25A24" or "SLC25A24 inhibitor" refer to an agent that can decrease the expression level and/or activity of SLC25A24, e.g. by at least 5%, at least 10%, at least 20%, at least 30%, at least 40%, at least 50%, at least 75%, at least 80%, at least 90%, at least 95%, at least 98%, at least 99% or more. It is preferred that an inhibitor of SLC25A24 inhibits SLC25A24 activity without substantially inhibiting other receptors (with the exception of SLC25A3) or activities. It is also preferred that the specific inhibitory activity occurs at a concentration that is not toxic to the subject. In some embodiments, a SLC25A24 inhibitor can decrease the level of SLC25A24 mRNA, the level of SLC25A24 polypeptide, and/or the activity of SLC25A24. SLC25A24 activity can be monitored, e.g., by measuring the TNAP activity, or by measuring the amount of phosphate transported into matrix vesicles. In some embodiments, a SLC25A24 inhibitor can specifically bind a SLC25A24 polypeptide. Irreversible or reversible inhibitors of SLC25A24 can be used in the methods disclosed herein. In one embodiment, an SLC25A24 inhibitor can inhibit TNAP activity. In one embodiment, an SLC25A24 inhibitor can inhibit the transport of phosphate into matrix vesicles.

As used herein, the term "SLC25A3" generally refers to a SLC25A3 polypeptide or a SLC25A3 polynucleotide. When referring to the inhibition of SLC25A3, it means, at a minimum, the inhibition of the expression level and/or activity of SLC25A3 that corresponds to NCBI Gene ID: 5250.

As used herein, the terms "inhibitor of SLC25A3" or "SLC25A3 inhibitor" refer to an agent that can decrease the expression level and/or activity of SLC25A3, e.g. by at least 5%, at least 10%, at least 20%, at least 30%, at least 40%, at least 50%, at least 75%, at least 80%, at least 90%, at least 95%, at least 98%, at least 99% or more. It is preferred that an inhibitor of SLC25A3 inhibits SLC25A3 activity without substantially inhibiting other receptors (with the exception of SLC25A24) or activities. It is also preferred that the specific inhibitory activity occurs at a concentration that is not toxic to the subject. In some embodiments, a SLC25A3 inhibitor can decrease the level of SLC25A3 mRNA, the level of SLC25A3 polypeptide, and/or the activity of SLC25A3. SLC25A3 activity can be monitored, e.g., by measuring TNAP (tissue non-specific alkaline phosphatase) activity, or by measuring the amount of phosphate transported into matrix vesicles. In some embodiments, a SLC25A3 inhibitor can specifically bind a SLC25A3 polypeptide. Irreversible or reversible inhibitors of SLC25A3 can be used in the methods disclosed herein. In one embodiment, an SLC25A3 inhibitor can inhibit TNAP activity. In one embodiment, an SLC25A3 inhibitor can inhibit the transport of phosphate into matrix vesicles.

As used herein, the terms "treat," "treatment," "treating," or "amelioration" refer to therapeutic treatments, wherein the object is to reverse, alleviate, ameliorate, inhibit, slow down or stop the progression or severity of soft-tissue calcification, e.g. cardiovascular calcification. The term "treating" includes reducing or alleviating at least one adverse effect or symptom of soft-tissue calcification. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the extent or amount of soft-tissue calcification is reduced, or the progression of soft-tissue calcification is slowed or halted. The term "treatment" of a disease also includes providing relief from the symptoms or side-effects of the disease (including palliative treatment).

As used herein, the term "prevent" or "prevention" refers to stopping, hindering, and/or slowing down the onset and/or development of calcification in soft-tissue calcification, or preventing further calcification in an individual who has some degree of calcification. In one embodiment, prevent is synonymous with inhibit.

As used herein, the term "pharmaceutical composition" refers to the one or more active agents in combination with a pharmaceutically acceptable carrier e.g. a carrier commonly used in the pharmaceutical industry.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, or intralesional.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The administration can be systemic or local.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples.

As used herein, the terms "protein" and "polypeptide" are used interchangeably to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The terms "decreased", "decrease", "reduce", "reduction", or "inhibit" are all used herein generally to mean a decrease by a statistically significant amount. For the avoidance of doubt, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a symptom, a protein level, or the functional activity of a protein is meant a statistically significant decrease in such level. The decrease can be, for example, at least 10%, at least 20%, at least 30%, at least 40% or more, and is preferably down to a level that prevents calcification progression within a soft tissue.

The term "statistically significant" or "significantly" refers to statistical significance and generally means a difference of two standard deviations (2SD) or more.

The terms "increased", "increase", or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material necessary or used in formulating an active ingredient or agent for delivery to a subject. Each carrier must be "acceptable" in the sense of being compatible with the other ingredients of the formulation and not injurious to the patient.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A shows TNAP activity in matrix vesicles isolated from smooth muscle cells cultured in control media (gray bar) or osteogenic media (red bars) and treated with scramble siRNA or siRNA targeted to SCaMC-1.

FIG. 2B shows mineralization in matrix vesicles isolated from smooth muscle cells cultured in control media (gray bar) or osteogenic media (red bars) and treated with scramble siRNA or siRNA targeted to SCaMC-1.

FIG. 4A shows that SCaMC-1 (green) is observed in a confocal fluorescence image of a calcified (red) human carotid plaque.

FIG. 4B shows SCaMC-1 (green) observed surrounding developing microcalcifications (red) in a confocal fluorescence image of a human carotid plaque.

FIG. 4C shows that SCaMC-1 (green) and TNAP (white) are closely associated in a confocal fluorescence image of a human carotid plaque.

DETAILED DESCRIPTION

Figure 1:
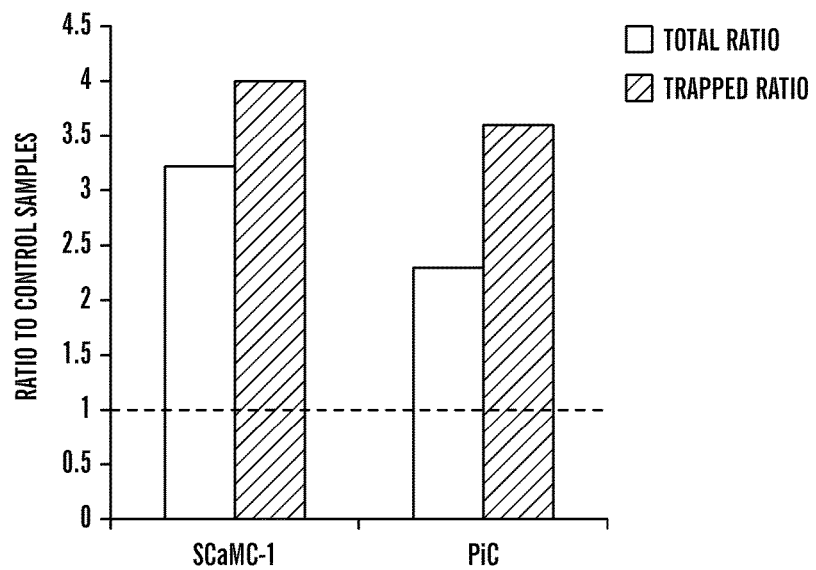
FIG. 1 shows mass spectrometry data of SCaMC-1 and PiC in matrix vesicles of calcifying smooth muscle cells normalized to control smooth muscle cells (shown by the dotted line at 1).

While the SLC25A24 and SLC25A3 proteins have been known in the art, neither of these proteins has previously been described as having a role in cardiovascular calcification or bone development.

The technology described herein is based, in part, on the discovery that SLC25A24 and SLC25A3 proteins are implicated in the calcification process of soft tissues. Accordingly, one aspect of the technology described herein provides a method of preventing or treating soft-tissue calcification in a subject in need thereof. In some embodiments, the soft-tissue calcification occurs in a soft tissue selected from the group consisting of an artery, a heart valve, an eye, a visceral organ, and skin. In one embodiment, the soft-tissue calcification is cardiovascular calcification. In one embodiment, the soft-tissue calcification is cranial calcification.

In some embodiments, the subject has diabetes.

In some embodiments, the subject has a renal disease such as chronic renal disease.

There are three major types of soft-tissue calcification: dystrophic, metastatic, and heterotopic. Soft-tissue calcification can be diagnosed by x-rays. For subjects with kidney stones, blood tests can be used to determine the overall kidney function. More details about soft-tissue calcification and diagnosis thereof can be found, for example, in "Diagnosis of Soft Tissue Calcification" by A. H. Elgazzar in Orthopedic Nuclear Medicine 2004, pp 197-210.

Either one or both of SLC25A24 and SLC25A3 can be targeted for the treatment of soft-tissue calcification. In some embodiments, the method comprises administering a therapeutically-effective amount of an SLC25A24 inhibitor to the subject. In some embodiments, the method comprises administering a therapeutically-effective amount of an SLC25A3 inhibitor to the subject.

In some embodiments, the method comprises administering a therapeutically-effective amount of an SLC25A3 inhibitor and an SLC25A24 inhibitor to the subject. In these embodiments, the administration of the SLC25A3 inhibitor can be before, concurrently, or after the administration of the SLC25A24 inhibitor.

An SLC25A24 inhibitor or SLC25A3 inhibitor can have an IC50 of less than 50 μM, e.g., an SLC25A24 inhibitor or SLC25A3 inhibitor can have an IC50 of from about 50 μM to about 5 nM, or less than 5 nM. For example, in some embodiments, an SLC25A24 inhibitor or SLC25A3 inhibitor has an IC50 of from about 50 μM to about 25 μM, from about 25 μM to about 10 μM, from about 10 μM to about 5 μM, from about 5 μM to about 1 μM, from about 1 μM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM.

In some embodiments, the SLC25A24 inhibitor is a small or large organic or inorganic molecule. In some embodiments, the SLC25A3 inhibitor is a small or large organic or inorganic molecule. As used herein, the term "small molecule" refers to a natural or synthetic molecule having a molecular mass of less than about 5 kD, organic or inorganic compounds having a molecular mass of less than about 5 kD, less than about 2 kD, or less than about 1 kD.

In some embodiments, the SLC25A24 inhibitor can be an anti-SLC25A24 antibody molecule or an antigen-binding fragment thereof. In some embodiments, the SLC25A3 inhibitor can be an anti-SLC25A3 antibody molecule or an antigen-binding fragment thereof. Suitable antibodies include, but are not limited to, polyclonal, monoclonal, chimeric, humanized, recombinant, single chain, $F_{ab}$, $F_{ab'}$, $F_{sc}$, $R_v$, and $F_{(ab')2}$ fragments. In some embodiments, neutralizing antibodies can be used as inhibitors of SLC25A24 or SLC25A3. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies. In general, an antibody molecule obtained from humans can be classified in one of the immunoglobulin classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies provide high binding avidity and unique specificity to a wide range of target antigens and haptens. Monoclonal antibodies useful in the practice of the methods disclosed herein include whole antibody and fragments thereof and are generated in accordance with conventional techniques, such as hybridoma synthesis, recombinant DNA techniques and protein synthesis.

The SLC25A24 or SLC25A3 polypeptide, or a portion or fragment thereof, can serve as an antigen, and additionally can be used as an immunogen to generate antibodies that immunospecifically bind the antigen, using standard techniques for polyclonal and monoclonal antibody preparation. Preferably, the antigenic peptide comprises at least 10 amino acid residues, or at least 15 amino acid residues, or at least 20 amino acid residues, or at least 30 amino acid residues.

Useful monoclonal antibodies and fragments can be derived from any species (including humans) or can be formed as chimeric proteins which employ sequences from more than one species. Human monoclonal antibodies or "humanized" murine antibody can also be used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction in the possibility of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is one option for minimizing the size of an antibody agent. ScFvs provide additional options for preparing and screening a large number of different antibody fragments to identify those that specifically bind. Techniques have been developed to display scFv molecules on the surface of filamentous phage that contain the gene for the scFv. scFv molecules with a broad range orantigenic-specificities can be present in a single large pool of scFv-phage library.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

Some anti-SLC25A24 antibodies and anti-SLC25A3 antibodies are commercially available from, for example, Abcam, Novus Biologicals, Sigma Aldrich, and Proteintech.

In some embodiments, the SLC25A24 inhibitor is a nucleic acid or a nucleic acid analog or derivative thereof, also referred to as a nucleic acid agent herein. In some embodiments, the SLC25A3 inhibitor is a nucleic acid or a nucleic acid analog or derivative thereof. In the context of this disclosure, the term "nucleic acid" refers to a polymer or oligomer of nucleotide or nucleoside monomers consisting of naturally occurring bases, sugars and intersugar linkages. The term "nucleic acid" or "oligonucleotide" or "polynucleotide" are used interchangeably herein and can mean at least two nucleotides covalently linked together. As will be appreciated by those skilled in the art, the depiction of a single strand also defines the sequence of the complementary strand. Thus, a nucleic acid also encompasses the complementary strand of a depicted single strand.

Without limitation, the nucleic acid agent can be single-stranded or double-stranded. A single-stranded nucleic acid agent can have double-stranded regions, e.g., where there is internal self-complementarity, and a double-stranded nucleic acid agent can have single-stranded regions. The nucleic acid can be of any desired length. In particular embodiments, nucleic acid can range from about 10 to 100 nucleotides in length. In various related embodiments, nucleic acid agents, single-stranded, double-stranded, and triple-stranded, can range in length from about 10 to about 50 nucleotides, from about 20 to about 50 nucleotides, from about 15 to about 30 nucleotides, from about 20 to about 30 nucleotides in length. In some embodiments, a nucleic acid agent is from about 9 to about 39 nucleotides in length. In some other embodiments, a nucleic acid agent is at least 30 nucleotides in length.

The nucleic acid agent can comprise modified nucleosides as known in the art. Modifications can alter, for example, the stability, solubility, or interaction of the nucleic acid agent with cellular or extracellular components that modify activity. In certain instances, it can be desirable to modify one or both strands of a double-stranded nucleic acid agent. In some cases, the two strands will include different modifications. In other instances, multiple different modifications can be included on each of the strands. The various modifications on a given strand can differ from each other, and can also differ from the various modifications on other strands. For example, one strand can have a modification, and a different strand can have a different modification. In other cases, one strand can have two or more different modifications, and the another strand can include a modification that differs from the at least two modifications on the first strand.

Single-stranded and double-stranded nucleic acid agents that are effective in inducing RNA interference are referred to as siRNA, RNAi agents, iRNA agents, or RNAi inhibitors herein. As used herein, the term "iRNA agent" refers to a nucleic acid agent which can mediate the targeted cleavage of an RNA transcript via an RNA-induced silencing complex (RISC) pathway.

In some embodiments, the SLC25A24 inhibitor is an antisense oligonucleotide. In some embodiments, the SLC25A3 inhibitor is an antisense oligonucleotide. One of skill in the art is well aware that single-stranded oligonucleotides can hybridize to a complementary target sequence and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H and thus preventing translation of target RNA. Alternatively, or in addition, the single-stranded oligonucleotide can modulate the expression of a target sequence via RISC mediated cleavage of the target sequence, i.e., the single-stranded oligonucleotide acts as a single-stranded RNAi agent. A "single-stranded RNAi agent" as used herein, is an RNAi agent which is made up of a single molecule. A single-stranded RNAi agent can include a duplexed region, formed by intra-strand pairing, e.g., it can be, or include, a hairpin or pan-handle structure.

In some embodiments, the targeting sequence for an siRNA that can be used to inhibit SLC25A24 is selected from the group consisting of CAGAUGAAUUCACG-GAAGA (SEQ ID NO: 1), GCAUAUGAACAGUA-CAAGA (SEQ ID NO: 2), GGAAAUGGUACAAAC-GUCA (SEQ ID NO: 3), GGUGCUGUCUCUCGAACAA (SEQ ID NO: 4), and a combination thereof.

In one embodiment, the small siRNA that can be used to inhibit SLC25A24 comprises nucleic acids of SEQ ID NO: 1-4.

In some embodiments, the small siRNA that can be used to inhibit SLC25A3 is selected from the group consisting of GGGCAUAUUUAACGGAUUC (SEQ ID NO: 5), UGGCGCACAUCACUAUAUU (SEQ ID NO: 6), GCAAUUGUUUCUCACCCUG (SEQ ID NO: 7), GCCAACACUUUGAGGGAUG (SEQ ID NO: 8), and a combination thereof.

In one embodiment, the small siRNA that can be used to inhibit SLC25A3 comprises nucleic acids of SEQ ID NO: 5-8.

siRNAs for inhibiting SLC25A24 or SLC25A3 are commercially available through vendors such as Life Technologies and OriGene.

In general, any method of delivering a nucleic acid molecule can be adapted for use with the nucleic acid agents described herein.

Methods of delivering RNA interference agents, e.g., an siRNA, or vectors containing an RNA interference agent, to the target cells, for uptake include injection of a composition containing the RNA interference agent, e.g., an siRNA, or directly contacting the cell with a composition comprising an RNA interference agent, e.g., an siRNA. In another embodiment, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agents may be used simultaneously. In one embodiment, specific cells are targeted with RNA interference, limiting potential side effects. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, inhibit annealing of single strands, stabilize single strands, or otherwise facilitate delivery to the target cell and increase inhibition of the target gene, e.g., SLC25A24 or SLC25A3. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

In some embodiments, the SLC25A24 and/or SLC25A3 inhibitor can also be a peptide, a peptidomimetic, a protein, a monosaccharide, a disaccharide, a trisaccharide, an oligosaccharide, a polysaccharide, a lipid, a glycosaminoglycan, an extract made from a biological material, or combinations thereof.

The SLC25A24 and/or SLC25A3 inhibitor can be administered in a pharmaceutical composition. In some embodiments, the pharmaceutical composition comprises a pharmaceutically-acceptable carrier and/or diluent. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutical compositions can be specially formulated for administration in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally the compounds described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes;

powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

The pharmaceutical compositions may be administered in any dose or dosing regimen. With respect to the therapeutic methods of the invention, it is not intended that the administration be limited to a particular mode of administration, dosage, or frequency of dosing.

The compounds of the present invention can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

In one embodiment, it may be desirable to administer the pharmaceutical compositions locally to the area in need of treatment; this may be achieved, for example, and not by way of limitation, by local infusion during surgery, topical application, e.g., by injection, by means of a catheter (e.g., a cardiac catheter, renal catheter, etc.), or by means of an implant, the implant being of a porous, non-porous, or gelatinous material, including membranes, such as sialastic membranes, fibers, or commercial skin substitutes. In some embodiments, for certain soft-tissue calcification site accessible by injection, an injection into the calcification site or its vicinity can be desirable.

In some embodiments, the pharmaceutical composition can be administered to a subject orally (e.g., in capsules, suspensions or tablets) or by parenteral administration. Conventional methods for oral administration include any one of the following; tablets, suspensions, solutions, emulsions, capsules, powders, syrups and the like are usable. Parenteral administration can include, for example, intramuscular, intravenous, intraarticular, intraarterial, intrathecal, subcutaneous, or intraperitoneal administration. The pharmaceutical composition can also be administered orally, transdermally, topically, by inhalation (e.g., intrabronchial, intranasal, oral inhalation or intranasal drops) or rectally.

When administering the pharmaceutical composition parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils. The term "Dosage unit" form as used herein refers to physically discrete units suited as unitary dosages for the subjects to be treated; each unit containing a predetermined quantity of active compound calculated to produce the desired therapeutic effect in association with the required pharmaceutical carrier.

An effective amount, e.g., a therapeutically effective dose of the compound disclosed herein may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising the compound disclosed herein can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

The term "effective amount" as used herein refers to the amount of a therapy needed to alleviate at least one or more symptoms of the disease or disorder (e.g., soft-tissue calcification), and relates to a sufficient amount of pharmaceutical composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

In some embodiments, an effective amount of an SLC25A24 inhibitor can be an amount which causes the level of SLC25A24 expression to decrease or, at least, to increase at a lower rate than it would be expected to increase in a subject not receiving the SLC25A24 inhibitor. In some embodiments, an effective amount can be an amount that decreases the amount of SLC25A24 polypeptide present in the subject and/or SLC25A24 polypeptide present in the matrix vesicles of the subject by a statistically significant amount.

In some embodiments, an effective amount of an SLC25A24 inhibitor can be an amount which reduces the activity of SLC25A24 polypeptide.

In some embodiments, an effective amount of an SLC25A3 inhibitor can be an amount which causes the level of SLC25A3 expression to decrease or, at least, to increase at a lower rate than it would be expected to increase in a subject not receiving the SLC25A3 inhibitor. In some embodiments, an effective amount can be an amount that decreases the amount of SLC25A3 polypeptide present in the subject and/or SLC25A3 polypeptide present in the matrix vesicles of the subject by a statistically significant amount.

In some embodiments, an effective amount of an SLC25A3 inhibitor can be an amount which reduces the activity of SLC25A3 polypeptide.

A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the composition being administered, and the condition of the patient, the particular condition of soft-tissue calcification to be treated, as well as the body weight or body surface area. The size of the dose is also determined by the existence, nature, and extent of any adverse side-effects that accompany the administration of a particular formulation, or the like in a particular subject. Therapeutic compositions are optionally tested in one or more appropriate in vitro and/or in vivo animal models of disease, and known to persons of ordinary skill in the art, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of the pharmaceutical composition at various concentrations, e.g., as applied to the mass and overall health of the patient.

The dosage can be determined by one of skill in the art and can also be adjusted by the individual physician in the event of any complication. Typically, the dosage of a composition comprising the compound disclosed herein can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although any known methods, devices, and materials may be used in the practice or testing of the invention, the methods, devices, and materials in this regard are described herein.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1: Validation of Phosphate Carriers as Calcification Targets

Physiological mineralization is initiated in bone and cartilage in association with matrix vesicles released by osteoblasts and chondrocytes (Anderson H C 2003). Due to this, it is suggested that such vesicles also play a significant role in pathological ectopic calcification (Shao J S, Cai J and Towler D A 2006). In medial calcification in patients with chronic kidney disease, vascular smooth muscle cells have already been identified to release calcifying matrix vesicles (30-300 nm) that serve as a nidus for mineral nucleation (Kapustin et al 2011; Reynolds et al 2009). While this is a feasible notion for medial calcification, in intimal calcification where macrophages are in abundance and smooth muscle cells are lacking, it is contemplated that macrophages play a greater role in the calcification process. It has been discovered that macrophages also release calcifying matrix vesicles, which are believed to provide new foci for hydroxyapatite nucleation resulting in the generation of microcalcifications. The generation of microcalcifications can occur in the presence of inflammation and lesions in the early stages of calcification; plaques such as these are often described as "spotty" calcifications (Aikawa E et al 2007). These 'spotty' calcifications located in the thin (<65 μm) fibrous cap overlying the necrotic core of atherosclerotic plaques are seen as dangerous, as they are more likely to cause plaque rupture due to debonding (Virmani R 2006) and lead to acute thrombosis and even sudden death due to fatal Myocardial infarction (Huang H 2001; Vengrenyuk et al 2006; Vengrenyuk et al. 2008; Hoshino T et al 2009). Therefore, halting the production of these microcalcifications can prevent the progression of intimal atherosclerotic calcification at the early stages of this disease and lessen the clinical burden associated with aortic valve calcification.

In mass spectrometry data, two members of the mitochondrial phosphate carrier family were identified that are increased in the matrix vesicles of calcifying human coronary artery smooth muscle cells—SLC25A3 (PiC) and SLC25A24 (SCaMC-1). An osteogenic cell culture medium was used to increase the calcific potential of human Coronary artery smooth muscle cell-derived matrix vesicles. This osteogenic medium is widely used to induce a calcific phenotype in cells (Hutcheson J D, Nat Rev Cardio, 2014). These proteins were also found to be trapped in the calcified matrix of the cell culture model. SCaMC-1 was 3.2 fold higher in matrix vesicles from human coronary artery smooth muscle cells cultured in osteogenic media with a 4-fold increase in the amount of protein trapped in the matrix under the calcifying conditions. Similarly, PiC was 2.3-fold higher in calcifying matrix vesicles and 3.5-fold higher in the calcified matrix (FIG. 1).

Further, adding additional phosphate to matrix vesicles isolated from the osteogenic culture produced a 100-fold increase in measured calcium phosphate mineral compared to the matrix vesicles isolated from control culture. This indicates that the calcific vesicles exhibit an increased sensitivity to phosphate that may be due to the presence of SLC25A24 and SLC25A3.

Neither of these proteins has previously been described in cardiovascular calcification or bone development; however, SCaMC-1 is closely related to a protein recently found to control mineral growth within the Japanese pearl oyster (Perovic et al. Biochemistry 2013). The structure of SCaMC-1 was recently described, including its function as an ATP/phosphate-Mg transporter (Yang et al. Structure 2014). Further, SCaMC-1 was shown to mediate the formation of calcium phosphate mineral, similar to that observed in vascular calcification, in the mitochondria of cancer cells (Traba et al. Cell death diff 2012). PiC expression has been shown to be controlled by microRNA-141 (Baseler et al. AJP-Cell Phys 2012), and microRNA-141 expression has been shown to control osteogenic mechanisms in aortic stenosis (Yanagawa et al. J thoracic cardio surg 2012). The data presented herein indicates a link between these two phosphate carriers (i.e., SLC25A3 and SLC25A24) and vascular calcification.

Figure 2A:
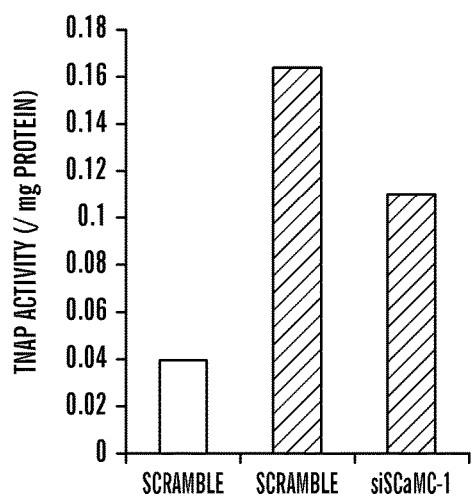
FIGS. 2A-2B show SCaMC-1 knockdown and matrix vesicle calcification potential.
Figure 2B:
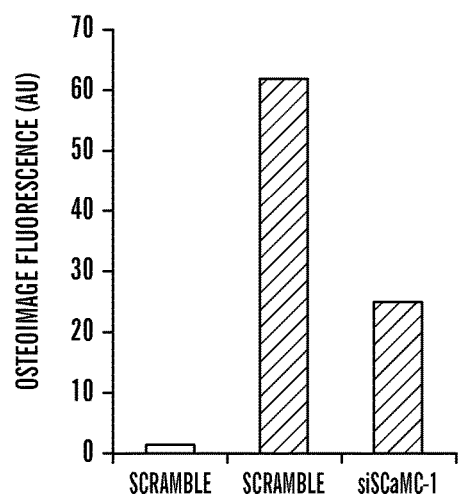

To test the role of SCaMC-1 in the system herein, vesicles were isolated from human coronary artery smooth muscle cells cultured in normal or osteogenic conditions for 14 days treated with either a scramble siRNA control or siRNA targeted to SCaMC-1. The siRNA used to target SCaMC-1 is a pool or combination of CAGAUGAAUUCACG-GAAGA (SEQ ID NO: 1), GCAUAUGAACAGUA-CAAGA (SEQ ID NO: 2), GGAAAUGGUACAAAC-GUCA (SEQ ID NO: 3), GGUGCUGUCUCUCGAACAA (SEQ ID NO: 4). Pooling at least two siRNAs is a known technique in the art. While each of the siRNAs is designed to target the same or different location on the target mRNA, the pooling technique can increase the likelihood of gene knockdown. siRNA targeted to SCaMC-1 are available from vendors such as Life Technologies. The vesicles were pelleted by ultracentrifugation at 100,000×g for 40 min and assayed for alkaline phosphatase (TNAP) activity (FIG. 2A). The Lonza OsteoImage kit was used to determine the mineralization of the matrix vesicles (FIG. 2B).

Osteogenic media resulted in a 4-fold increase in TNAP activity and a 20-fold increase in mineralization compared to control media in the scramble treated samples. The siRNA targeted to SCaMC-1 led to a slight reduction in measured TNAP activity and a 2.5-fold reduction in mineralization compared to the scramble treated group.

Figure 3:
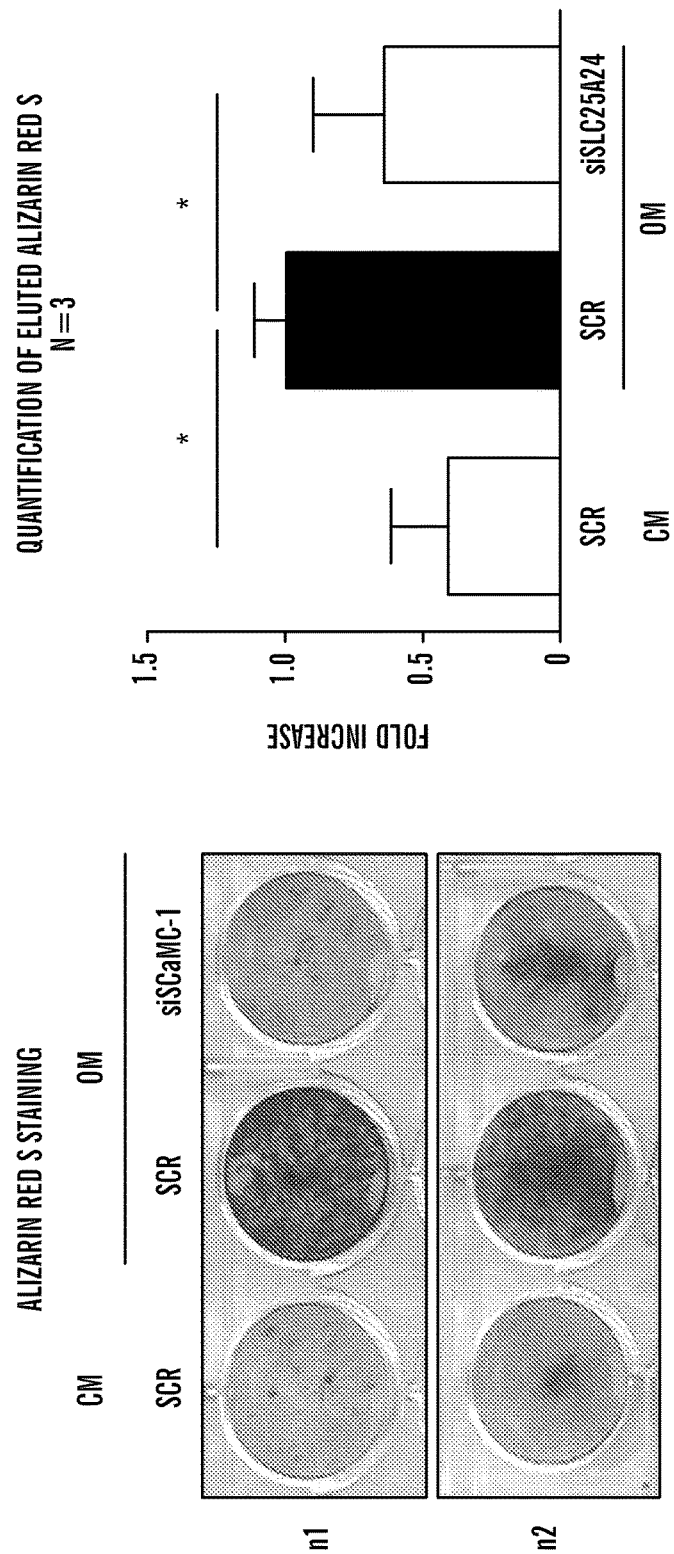
FIG. 3 shows Alizarin red s staining of smooth muscle cells cultured in control media or osteogenic media and treated with scramble siRNA or siRNA targeted to SCaMC-1.

To further assess the ability of SCaMC-1 inhibitors to prevent calcification, alizarin red S staining was performed to measure calcium deposition in human coronary artery smooth muscle cells after 21 days in control (CM) osteogenic (OM) culture treated with either a scramble siRNA control or siRNA targeted to SCaMC-1. FIG. 3 shows representative images of the staining as well as quantification of the alizarin red S measured using an absorbance reading of the solution eluted from the culture.

Figure 4:
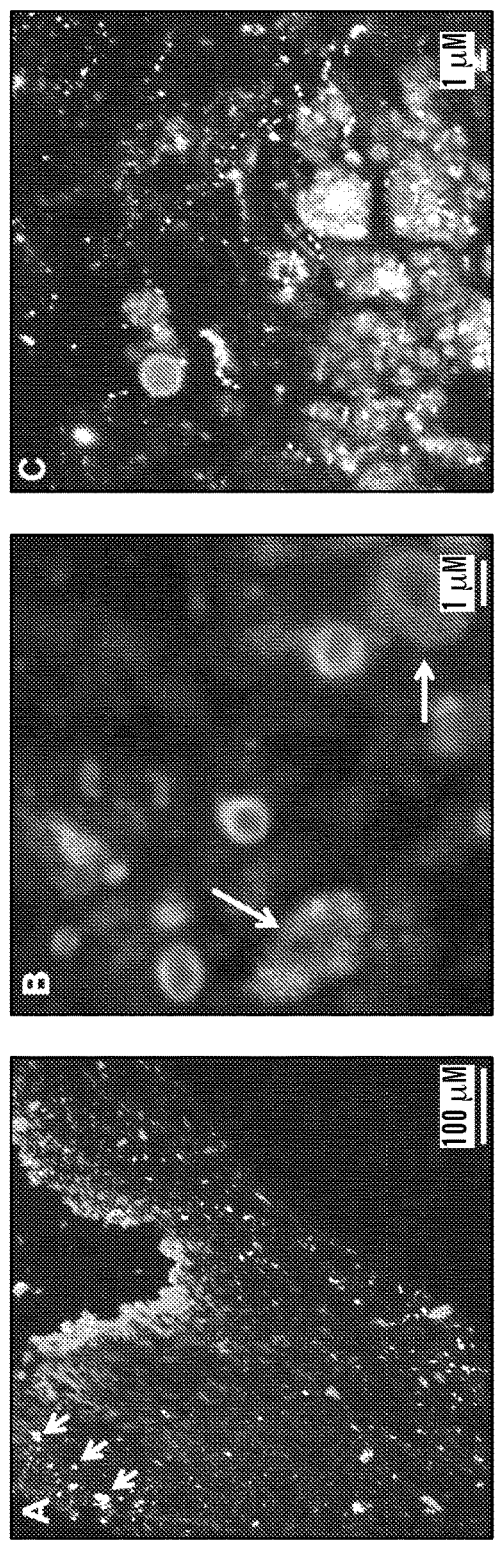
FIGS. 4A-4C show immunofluroescence analysis of relationship between SCaMC-1, calcification, and TNAP.

The smooth muscle cells cultured in OM demonstrated a 2-fold increase in alizarin red S staining. The calcium deposition was significantly reduced in three different donors by siRNA knockdown of SCaMC-1. To assess the expression of SCaMC-1 in vivo we performed immunofluorescent staining on human carotid plaques. Expression of SCaMC-1 was observed surrounding calcified tissue (FIG. 4A, arrows). A high magnification confocal image of SCaMC-1 and calcium tracer revealed SCaMC-1 surrounding regions that appear to be developing microcalcifications (FIG. 4B). These SCaMC-1 positive structures were found to be in close association with a known marker and driver of calcification, tissue non-specific alkaline phosphatase (FIG. 4C).

These results demonstrate that SCaMC-1 is a viable therapeutic target for the treatment of vascular calcification.

A pool of GGGCAUAUUUAACGGAUUC (SEQ ID NO: 5), UGGCGCACAUCACUAUAUU (SEQ ID NO: 6), GCAAUUGUUUCUCACCCUG (SEQ ID NO: 7), GCCAACACUUUGAGGGAUG (SEQ ID NO: 8) can be used to target the SLC25A3 gene.

Figure 5:
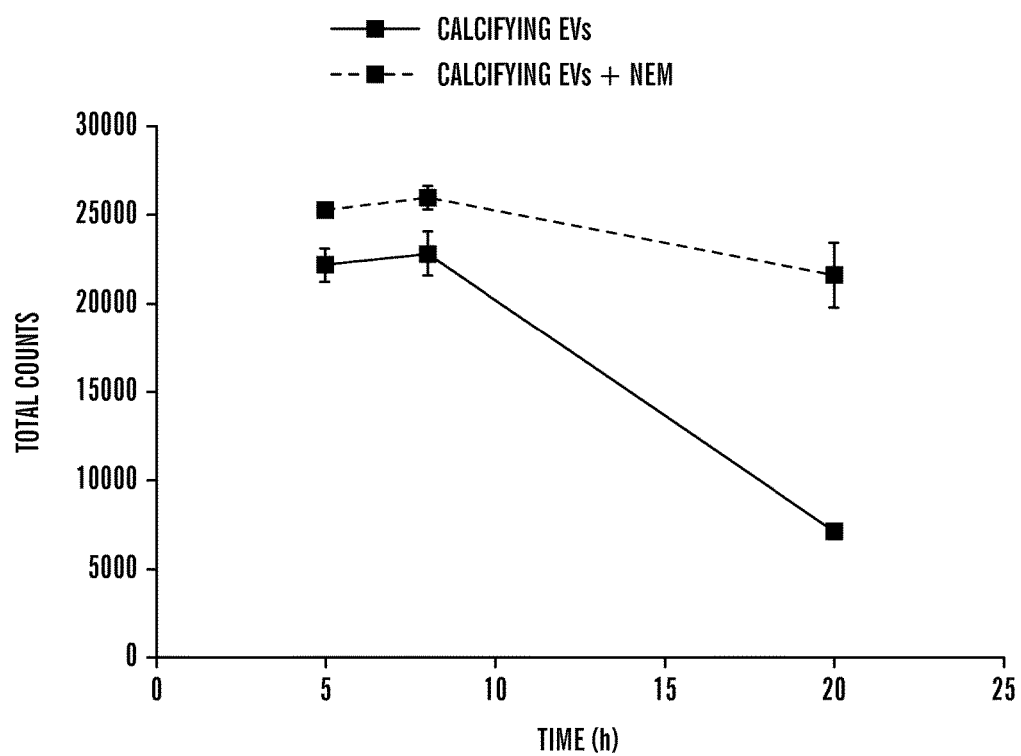
FIG. 5 shows data related to calcifying extracellular vesicles (EVs) incubated with or without 100 μM N-ethylmaleimide (NEM) for 20 h in the EX300 particle counter.

In addition, experiments were performed with N-ethylmaleimide (NEM), which has been shown to non-specifically inhibit mitochondrial phosphate carriers such as SCaMC-1 and PiC. Calcification has been previously linked to aggregation of extracellular vesicles. Therefore, vesicles were collected from smooth muscle cells cultured in calcifying conditions and incubated in cell-free conditions at 37° C. within a particle counting device. These data show that as the vesicles aggregate, fewer particles are counted. Aggregation of calcifying vesicles was observed by a reduction in total particles counted from 8 h to 20 h of incubation, as shown in FIG. 5. The addition of 100 µM NEM mitigated the reduction in vesicle counts. Without wishing to be bound by theory, it is hypothesized that this reduction is due to the inhibition of phosphate carriers on the vesicles, which blocks phosphate transport into the vesicles, and in turn preventing mineral formation. These data indicate that phosphate carriers are required to mediate the phosphate transport into vesicles that is necessary for calcification.

The invention claimed is:

1. A method of treating soft-tissue calcification in a coronary artery or heart valve in a subject, the method comprising administering a therapeutically-effective amount of an inhibitor of solute carrier family 25 member 24 (SLC25A24) to the subject, wherein the SLC25A24 inhibitor comprises at least one small interfering RNA (siRNA) comprising a targeting sequence selected from the group consisting of: CAGAUGAAUUCACGGAAGA (SEQ ID NO: 1), GCAUAUGAACAGUACAAGA (SEQ ID NO: 2), GGAAAUGGUACAAACGUCA (SEQ ID NO: 3), and GGUGCUGUCUCUCGAACAA (SEQ ID NO: 4) wherein the SLC25A24 inhibitor decreases the expression level of SCL25A24.

2. The method of claim 1, further comprising administering a therapeutically-effective amount of an inhibitor of solute carrier family 25 member 3 (SLC25A3) to the subject.

3. The method of claim 1, wherein the subject is a mammal.

4. The method of claim 3, wherein the mammal is a human.

* * * * *